United States Patent [19]

Wagner et al.

[11] Patent Number: 5,435,182

[45] Date of Patent: Jul. 25, 1995

[54] METHOD AND APPARATUS FOR DETERMINING AT LEAST ONE PHYSICAL PARAMETER OF ACCUMULATOR ELECTRODE PLATES

[75] Inventors: Rainer Wagner, Dortmund; Peter Scharf; Eberhard Nann, both of Soest, all of Germany

[73] Assignee: Hagen Batterie AG, Soest, Germany

[21] Appl. No.: 219,850

[22] Filed: Mar. 30, 1994

[30] Foreign Application Priority Data

Mar. 31, 1993 [DE] Germany ................ 43 10 541.6

[51] Int. Cl.⁶ ............................................ G01N 9/08
[52] U.S. Cl. ........................................ 73/437; 73/433
[58] Field of Search ................ 73/433, 434, 435, 436, 73/437

[56] References Cited

U.S. PATENT DOCUMENTS

| B 528,401 | 2/1976 | Appleford et al. | 73/437 |
|---|---|---|---|
| 3,747,416 | 7/1973 | Wommack | 73/437 |
| 4,372,405 | 2/1983 | Stuart | 73/437 |

*Primary Examiner*—Richard E. Chilcot, Jr.
*Assistant Examiner*—Max H. Noori
*Attorney, Agent, or Firm*—Townsend and Townsend Khourie and Crew

[57] ABSTRACT

A method for determining at least one physical parameter of accumulator electrode plates, such as the true plate thickness $P_d$, the apparent density $D_s$ of the active material, the true density $D_w$ of the active material, the pore volume $P_a$, the porosity $P_0$ of the active material or the pore structure, is performed such that, by means of various weighings, the weight ($G_{FP}$) of a liquid plate is determined instead of the weight of a real electrode plate, and, from this value, the desired physical parameter is obtained which is used for controlling the production process.

14 Claims, 1 Drawing Sheet

METHOD AND APPARATUS FOR DETERMINING AT LEAST ONE PHYSICAL PARAMETER OF ACCUMULATOR ELECTRODE PLATES

BACKGROUND OF THE INVENTION

The invention relates to a method and to an apparatus for determining at least one physical parameter of accumulator electrode plates, such as the true plate thickness, the apparent density, the true density, the pore volume and/or the porosity, and/or the pore structure.

Just as in conventional lead sulfuric acid accumulators, positive and negative electrode plates are used in fleece-bound, recombinable lead sulfuric acid accumulators which substantially comprise a metal grid, which serves as a material carrier and for carrying away the electrical current, and the positive or negative active material. In order to achieve high capacities and/or high discharge currents, a large contact surface between the active material, which is made of lead dioxide on the positive side and lead on the negative side, and the sulfuric acid serving as the electrolyte, is necessary, since the generally known electrochemical reactions in lead sulfuric acid accumulators takes place substantially at these contact surfaces. For this reason, the active materials must have a porous structure.

Furthermore, it must be ensured that during discharge of the accumulator the sulfuric acid itself takes part in the electrochemical reactions which are taking place so that it is used up. Consequently, the hollow volumes in the active materials are also of import as storage space for the quantity of sulfuric acid required during a discharge.

Moreover, the lead sulfate which forms both on the positive and the negative plates during discharge has a larger volume than the end products so that a reduction of the pore volume occurs during discharge. This is highly disadvantageous for the transport of further sulfuric acid out of the space between the electrode plates into the electrode plates. For these reasons, the active materials must have a suitable porous structure, i.e. the proportion of hollow volume to entire volume of the active material must attain a particular value, or the apparent density and the true density of the active material must have a particular ratio, in order to allow all the transport processes coupled with the electrochemical reaction to proceed at the required speed.

Apparent density is understood to mean the quotient of the weight of the material and its total volume including the porous volume. The true density of the material is obtained by dividing its weight by the total volume less the pore volume.

It is thus of major importance during the manufacture of the active material from positive and negative accumulator electrode plates to produce an optimum porous structure. By optimum structure it is meant that the proportion of hollow volume in the active material should indeed be relatively large but not too large since otherwise the lifetime of the electrode plates is reduced.

In recombination batteries comprising glass-fiber separators, the acid fill level of the separators assumes a key importance for the performance of the accumulator. Consequently, the plate thicknesses must correspond exactly to the design values in order to maintain the set pressing power and the free pore volume of the separator constant. For this, it is particularly important to determine the true plate thickness, i.e. the thickness which is obtained from the true volume taking into to account all the uneven features of the plates such as, for example surface indentations or fissures.

There are a large number of parameters used in the course of the manufacturing process which later affect the structure of the active material and also the plate thickness. The most important are the recipé as well as the conditions during the manufacture of the moist pastes and during its incorporation into the grid material, and also the parameters used during maturing, drying and formation of the plates.

Numerous methods are known for determining the plate thickness. A very simple method consists of a manual measurement with Vernier callipers or with some other mechanical thickness measuring device.

It is also already known (DE 38 26 516 A1) to use a laser thickness measurement device for determining the thickness of freshly pasted electrode plates, although this involves a high level of technical complexity.

All these known methods have the common disadvantage that the measurement result obtained for the plate thickness is not the true plate thickness, but is rather a too large a plate thickness, this being particularly important for recombination batteries. The reason for this is the rough and non-uniform surface of the electrode plates which plays a primary roll in raising the surface during the thickness measurement.

The conventional measurement methods also do not allow anything to be ascertained about the structure of the active material.

As a result of the complexity and imprecision of the known measurement methods, investigations of the porous structure of the active material for monitoring the production steps are not carried out during the manufacture of the electrode plates. That is to say, the known measurement methods are not employable as production controls or as dimensions for production control.

Methods for characterisation of porous solid bodies with regard to the proportion of hollow volume in the entire body and the structure of the hollow volumes themselves, such as mercury porosimetry or porosity measurements are know from the following literature: Drotschmann, C. Bleiakkumulatoren, Weinheim 1951, page 132; Drotschmann, C. Batterien 11 (1943), page 207; Manegold, E. Kolloid-Zeitschrift 81 (1937); Samsonov, P. D. Kuznezova, N. G., Journal angewandten Chemie 4 (1941), page 318.

These relate exclusively to laboratory methods which are inherently unsuited to monitoring of the production since they are slow and require complicated apparatus, and, furthermore, the deployment of qualified personnel.

In mercury porosimetry, the penetration of a non-moistening liquid in a porous body is measured in dependence on the liquid pressure, and from this the size and distribution of the pore volumes is deduced. These methods are of considerable complexity as they use high pressure apparatus. Moreover, the investigations can only be carried out by specially trained personnel and are not straightforwardly applicable to negative active materials. The displacement methods in which one measures the amount of liquid which has penetrated into the porous sample body and determines the volume of the entire body which is filled with liquid via a bouyancy measurement are also very complicated and, furthermore, the analysis time amounts to at least 24 hours.

Moreover, the methods known hitherto have the disadvantage of using measurement liquids which have different physical properties, for instance a different surface tension than sulfuric acid, and thus occupy different pore spaces than sulfuric acid.

SUMMARY OF THE INVENTION

The object of the invention is to provide a method and an apparatus in accordance with the preamble of claim 1 with which an automatic determination of the mechanical parameters of accumulator electrode plates is possible, in particular an automatic determination of the structure of the active material and of the true plate thickness. The automatic determination should be performable during the accumulator production process and usable for its control. In particular, the method and apparatus in accordance with the invention should be suited to the production of recombination accumulators.

The underlying concept of the invention is that instead of determining the weight of a real electrode plate, one determines that of a substitute liquid plate via the weighing steps and method steps described below, substitute liquid plate having the same area as the real electrode plate but a uniform thickness which is in agreement with that of the true, i.e. the average plate thickness of the electrode plate.

With the invention, it is possible to determine the true plate thickness even for electrode plates whose pores are already partly or wholly filled with liquid, as is the case after pasting or pre-drying.

If, however, the invention is used for electrode plates in a dry state, one proceeds in accordance with claim 2.

With this weight, the true plate thickness can then be very accurately determined an accordance with claim 3.

Of special import is that, the liquid used is physically and/or chemically similar to the electrolyte. The measurement liquids should thus have, in particular, a surface tension which is the same or similar to that of the electrolyte used subsequently, for instance to that of sulfuric acid, so that the measurement liquid fills the pores of the active material in the same manner as the electrolyte. The true pore volume in accordance with claim 5 can only be obtained if the measurement liquid has physical properties which approach those of the accumulator electrolyte, for example sulfuric acid.

DESCRIPTION OF THE PREFERRED EMBODIMENTS

Figure 1:
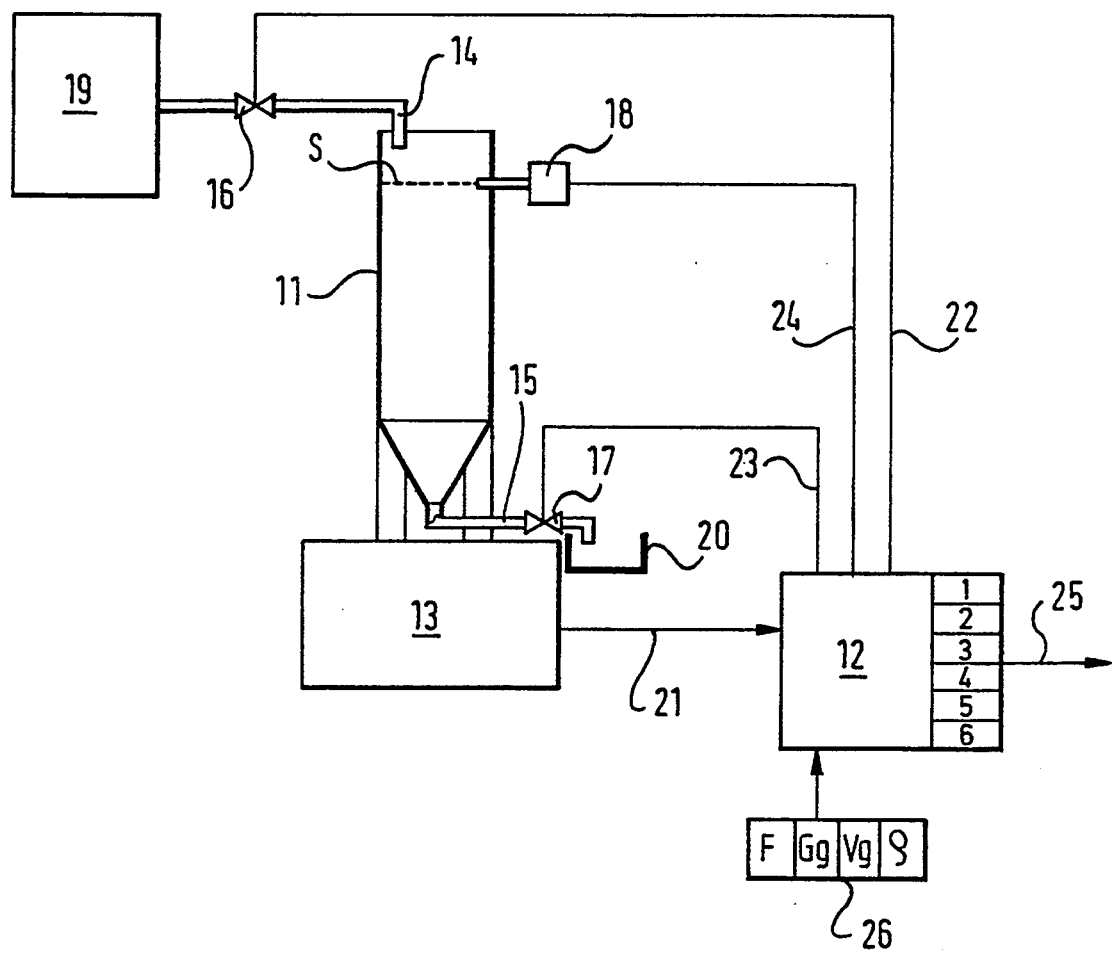
FIG. 1 a schematic reproduction in the form of a block diagram of an apparatus suitable for performing the method of the invention.

In accordance with FIG. 1, the apparatus comprises a weigher 13 on which a container 11 for receipt of accumulator electrode plates is arranged. A liquid supply line 14 discharges into the upper end of the container 11 and is connected to a liquid storage container 19 via a magnetic valve 16.

A liquid removal line 15 branches off at the lower end of the container 11 and is connected to a magnetic valve 17. By opening the magnetic valve 17, liquid present in the container 11 can be passed through the liquid removal line 15 into the collection container. After the collection container 20 has been filled up, it can be emptied to refill the storage container 19 with liquid. The measurement liquid present in the storage container 19 can thus be used many times.

A liquid level switch 18 is arranged in the upper region of the container 11 which is responsive to a reference liquid level S in the container 11.

An electrical signal appears at the output of the weigher 13 which is representative of the weight of the container 11 including contents, and which is connected via a lead 21 to control electronics 12. Moreover, the control electronics 12 is connected via leads 22, 23, 24 to the magnetic valve 16, the magnetic valve 17 and the liquid level switch 18 respectively.

An output signal is delivered at the output 25 of the control electronics 12 which is determined by the weighings and calculations undertaken in accordance with the invention, and is used for controlling the course of the production during manufacture of the accumulator electrode plates.

When the liquid in the container 11 has reached the reference level S, the liquid in the container 11 occupies a predetermined volume.

In accordance with the preferred embodiment, the course of the program in the method in accordance with the invention is as follows:

Initially, the weight $G_{fl}$ of the measurement liquid introduced in the container 11 from the storage container 19 is obtained for the reference liquid level S, this being performed without there being anything else in the container 11 apart from the measurement liquid. This can, for example, be performed by initially determining the weight of the empty container 11, and by subsequently filling the container 11 up to the reference liquid level S with liquid from the storage container 19 by opening the magnetic valve 16. When the reference liquid level S is reached, the liquid level switch 18 signals this to the control electronics 12 which, as a result, instantaneously closes the magnetic valve 16 so that a known volume of liquid is present in the container 11. The weight $G_{fl}$ of the liquid present in the container 11 can thus be calculated by taking the difference.

Subsequently, one or a plurality of accumulator electrode plates are taken from the ongoing production, placed into the empty, dry container 11 and weighed in their dry state. The dry weight $G_c$ is stored in the control electronics 12 which, for example can be realised with a microprocessor.

Subsequently in the second working cycle, the container 11 is filled up to the reference liquid level S with measurement liquid from the storage container 19 by opening the magnetic valve 16. It takes some time for the active material of the electrode plates to suck up the amount of liquid defined by the pore volume. During this time, liquid must be continually added from the storage container 19 in order to maintain the reference liquid level S. This topping up can take place periodically or also in one go after filling of the pore volume.

The time taken to completely fill the pores with liquid depends on the pore structure of the active material. Different pore structures thus have different filling speeds. This can be detected by carrying out a measurement of the pore structure appreciably before the complete saturation of the pores with liquid by determining the weight $G_d$ of the contents of the container 11 at the reference liquid level S at a defined short period after immersing the dry electrode plates in the liquid, and to determine from this an apparent short period porosity $P'_0$ in the manner described in more detail below.

After it is safe to assume that the pore volume of the active material is filled with measurement liquid to the furthest possible extent, the weight $G_a$ of the contents of the container 11 with the electrode plates arranged therein, and of the liquid filled up to the reference liquid level S is measured, registered by the control electronics 12, and stored.

As soon as this has taken place, the magnetic valve 17 is opened in the next working cycle by the control electronics 12, and the measurement liquid is completely drained from the container 11 into the collection container 20. Subsequently, the weight $G_b$ of the contents of the container 11 is determined and stored in the control electronics 12, the container 11 now only containing the wet electrode plates but otherwise no liquid.

The values of the plate area F, the weight of the grid $G_g$, the volume of the grid $V_g$ and the density $\rho$ of the measurement liquid are also stored in the control electronics. These values can be entered into the control electronics 12 prior to carrying out the method of the invention by a suitable input device 26.

The control electronics 12 now calculate one or more of the following physical parameters of the plates on the basis of the corresponding hardware or software provided therein in accordance with the following formulae:

1. True plate thickness $P_d$:
$$\frac{G_{fl} - (G_a - G_b)}{\rho \cdot F}$$

2. Apparent density $D_s$ of the active material:
$$\frac{G_c - G_g}{\frac{G_{fl} - (G_a - G_b)}{\rho} - V_g}$$

3. Pore volume $P_v$:
$$\frac{G_b - G_c}{\rho}$$

4. True density $D_w$ of the active material:
$$\frac{G_c - G_g}{\frac{G_{fl} - (G_a - G_b) - (G_b - G_c)}{\rho} - V_g}$$

5. Porosity $P_o$:
$$\frac{\frac{G_b - G_c}{\rho}}{\frac{G_{fl} - (G_a - G_b)}{\rho} - V_g}$$

6. Pore filling:
$$\frac{P'_0}{P_0}$$

$P'_o$ being the apparent short period porosity determined after a short time at which the pores are only partly filled with liquid, for the determination of which a weighing of the container 11 with the electrode plates which are only partially filled with liquid is performed at the reference liquid level S, and the corresponding weight $G_d$ is determined. For determining the short period porosity $P'_0$ the weight $G_a$ is replaced by $G_d$ in formula 5.

The corresponding calculation steps in the control electronics 12 are indicated in the FIGURE with 1, 2, 3, 4, 5 and 6.

The output lead 25 of the control electronics 12 can comprise a plurality of wires for transferring the individual parameter signals. The transfer may however also take place in serial by time multiplexing.

The reference values of the mechanical parameters 1, 2, 3, 4 and 5 can be stored in the control electronics 12 and compared with the actual values received there. Depending on whether the actual values deviate from the reference values, corresponding control signals can be sent via the output lead 25 to the individual production stages in order to make changes in the production which will lead to a convergence of the real values to the desired reference values.

A practical example for determining the mechanical parameters is given in the following:

Formed, positive electrode plates with a lead grid and lead dioxide as the active material of a recombination accumulator with a glass-fiber separator and with the following dimensions was used:

plate area F: 150 cm$^3$
grid weight $G_g$: 119 g
grid volume $V_g$: 11 cm$^3$

Water was used as the measurement liquid so that the density $\rho$ could be taken as 1.

These values were input into the control electronics 12 via the input device 26.

Subsequently, the various weights were determined as follows by means of the weigher 13, and stored in the control electronics 12:

$G_{fl}$ = 1045 g
$G_c$ = 257 g
$G_a$ = 1276 g
$G_b$ = 276 g
$G_d$ = 1273 g

The following values, which are determined by the control electronics 12, are obtained by substituting into the above formulae 1, 2, 3, 4 and 5 respectively:

True plate thickness $P_d$: 0.30 cm

A control measurement with Vernier callipers obtained a value of 0.32 cm.

Apparent density $D_s$: 4.06 g/cm$^3$
Pore volume $P_v$: 19.0 cm$^3$
True density $D_w$: 9.20 g/cm$^3$
Porosity $P_0$: 56%. $P'_0$: 51% $P'_0/P_0$ = 0.91

The value of 9.20 g/cm$^3$ determined as the true density deviates from the literature value of lead dioxide of 9.40 g/cm$^3$ because circa 2% PbSO$_4$ is present and because pores are present in the PbO$_2$ which are closed and not accessible to the measurement liquid. The theoretical porosity of 58% also deviates from the measured porosity, wherein the measured porosity corresponds to the real value achievable for sulfuric acid. The advantage of the method of the invention thus lies in the fact that it determines the real and not the theoretical electrolyte absorbency of the active material.

Alongside their simplicity, the advantages in applying the method and apparatus of the invention lie above all in the high flexibility. The fact that the accumulator electrode plates can be non-destructively tested means that the number of tested items can be varied to a large degree as necessary. The duration of the test program can also be altered depending on which of the parameters of the electrode plates to be investigated are particularly important. So, for instance, when only the true plate thickness needs to be determined, a very short program is sufficient.

Further, the accumulator electrode plates can be examined after different production steps. It is thus possible to determine the true plate thickness directly after pasting or after pre-drying. Investigations of the pore structure of the active material and determining of the plate thickness are possible after maturing and drying and also after the formation of positive and negative electrode plates. The reactions between the measurement liquid and the negative material which take place to a small extent have no influence on the precision of the measurement method.

We claim:

1. A method for determining at least one physical parameter of an accumulator electrode plate designed for functioning in an electrolyte, said accumulator electrode plate having a defined surface and comprising a metal grid made of lead and having a weight ($G_g$) and volume ($V_g$) and porous active material arranged thereon, the method comprising the steps of:

providing a container with a liquid filled to a preset level, the liquid having a density (p);

determining a weight ($G_{fl}$) of the liquid in the container;

immersing a dry electrode plate having pores into the liquid in the container;

allowing the liquid to penetrate the pores of the dry electrode plate until the pores are at least substantially saturated with liquid to form a saturated electrode plate;

adjusting the liquid level in the container back to the preset level after the liquid has started to penetrate the pores of the dry electrode plate;

determining a weight ($G_a$) of the liquid and the saturated electrode plate;

discharging the liquid from the container;

determining a weight ($G_b$) of the saturated electrode plate;

calculating a difference between the weight ($G_a$) and the weight ($G_b$) to obtain an interim weight $G_{(1)}$;

calculating a difference between the interim weight ($G_1$) and the weight ($G_{fl}$) of the liquid to obtain a weight $G_{(FP)}$ of a substitute electrode plate made of the liquid; and determining said at least one physical parameter of the accumulator electrode plate with the weight ($G_{FP}$) of the substitute electrode plate made of the liquid.

2. The method of claim 1 further comprising dividing the weight ($G_{FP}$) by the density (p) of the liquid and an area (F) of the accumulator electrode plate to obtain a true plate thickness ($P_d$).

3. A method for determining at least one physical parameter of an accumulator electrode plate designed for functioning in an electrolyte, the accumulator electrode plate having a defined surface and comprising a metal grid made of lead and having a weight ($G_g$) and volume ($V_g$) and porous active material arranged thereon, the method comprising the steps of:

introducing a dry electrode plate into a container;

determining a dry weight ($G_c$) of the dry electrode plate and the container;

removing the dry electrode plate from the container;

filling the container with a liquid to a preset level, the liquid having a density (p);

determining a weight ($G_{fl}$) of the liquid;

immersing a dry electrode plate having pores into the liquid in the container;

allowing the liquid to penetrate the pores of the dry electrode plate;

adjusting the liquid level in the container back to the preset level after the pores are at least substantially saturated with liquid;

determining a weight ($G_a$) of the liquid and the saturated electrode plate;

discharging the liquid from the container;

determining a weight ($G_b$) of the saturated electrode plate;

calculating a difference between the weight ($G_a$) and the weight ($G_b$) to obtain an interim weight $G_{(1)}$;

calculating a difference between the interim weight ($G_1$) and the weight ($G_{fl}$) of the liquid to obtain a weight $G_{(FP)}$ of a substitute electrode plate made of the liquid; and determining said at least one physical parameter of the accumulator electrode plate with the weight ($G_{FP}$) of the substitute electrode plate made of the liquid.

4. The method of claim 3 further comprising the steps of:

calculating a difference between the dry weight ($G_c$) and the weight ($G_g$) of the metal grid to obtain a first interim value;

dividing the weight ($G_{fp}$) of the substitute electrode plate by the density (p) of the liquid to obtain a second interim value;

subtracting the volume ($V_g$) of the metal grid from the second interim value to obtain a third interim value; and dividing the first interim value by the third interim value to obtain an apparent density ($D_s$) of the accumulator electrode plate.

5. The method of claim 3 further comprising the steps of:

subtracting the dry weight ($G_c$) from the weight ($G_b$) to obtain a first interim value; and dividing the first interim value by the density (p) of the liquid to obtain a pore volume ($P_v$) of the accumulator electrode plate.

6. The method of claim 5 further comprising the steps of:

subtracting the first interim value from the weight ($G_{fp}$) to obtain a second interim value;

dividing the second interim value by the density (p) of the liquid to obtain a third interim value;

subtracting the volume ($V_g$) of the metal grid from the third interim value to obtain a fourth interim value; and dividing a difference between the weight ($G_b$) and the dry weight ($G_c$) by the fourth interim value to obtain a true density ($D_w$) of the accumulator electrode plate.

7. The method of claim 5 further comprising the steps of:

dividing the weight ($G_{fp}$) by the density (p) of the liquid to obtain a second interim value;

subtracting the volume ($V_g$) of the metal grid from the second interim value to obtain a third interim value; and dividing the pore volume ($P_v$) by the third interim value to obtain a porosity ($P_o$) of the accumulator electrode plate.

8. The method of claim 7 further comprising the steps of:

determining a weight ($G_d$) of the container, the dry electrode plate and the liquid when the pores of the dry electrode plate are partially filled with the liquid;

calculating a short period porosity ($P'_o$) of the material based on the weight ($G_d$); and dividing the porosity ($P_o$) by the short term porosity ($P_o$) to obtain a pore filling of the accumulator electrode plate.

9. The method of claim 3 wherein control electronics implement the determining and calculating steps.

10. The method of claim 3 wherein the electrolyte is sulfuric acid and the liquid is an aqueous sulfate solution.

11. The method of claim 3 wherein the accumulator electrode plate is a recombination accumulator with a glass-fiber separator.

12. An apparatus for determining at least one physical parameter of an accumulator electrode plate designed for functioning in an electrolyte, said accumulator electrode plate having a defined surface and comprising a metal grid made of lead and having a weight ($G_g$) and volume ($V_g$) and porous active material arranged thereon, the apparatus comprising:

a container;

means, coupled to the container, for supplying a liquid up to a preset level in the container, the liquid having a density and a weight ($G_{fl}$);

means, coupled to the container, for immersing a dry electrode plate having pores into the liquid in the container such that the liquid substantially saturates the pores to form a saturated electrode plate;

an actuator, operatively coupled to the container and the liquid supply means, for actuating the liquid supply means so that the liquid returns to the preset level after the pores of the electrode plate are saturated;

a weigher mounted below the container for determining a weight ($G_a$) of the container, the liquid and the saturated electrode plate;

means, coupled to the container, for removing the liquid from the container, the weigher being adapted to determine a weight ($G_b$) of the container and the saturated electrode plate after the liquid has been removed from the container; and electronics means, operatively coupled to the supply and removal means and the weigher, for calculating a difference between the weight ($G_a$) and the weight ($G_b$) to obtain an interim weight $G_{(1)}$ and then calculating a difference between the interim weight ($G_1$) and the weight ($G_{fl}$) of the liquid to obtain a weight $G_{(FP)}$ of a substitute electrode plate made of the liquid, wherein said at least one physical parameter of the accumulator electrode plate can be determined based on the weight ($G_{FP}$) of the substitute electrode plate made of the liquid.

13. The method of claim 1 wherein adjusting step is continuously performed while the liquid is penetrating the pores of the dry electrode plate.

14. The method of claim 1 wherein the adjusting step is performed after the pores of the dry electrode plate have been substantially saturated by the liquid.

* * * * *